(12) United States Patent
Haga et al.

(10) Patent No.: US 9,156,857 B2
(45) Date of Patent: Oct. 13, 2015

(54) DIETHYLZINC COMPOSITION, METHOD FOR HEAT STABILIZATION, AND COMPOUND FOR HEAT STABILIZATION

(75) Inventors: Kenichi Haga, Yamaguchi (JP); Shizuo Tomiyasu, Yamaguchi (JP); Kohichi Tokudome, Yamaguchi (JP); Kouji Toyota, Yamaguchi (JP); Koichiro Inaba, Yamaguchi (JP)

(73) Assignee: TOSOH FINECHEM CORPORATION, Yamaguchi (JP)

( * ) Notice: Subject to any disclaimer, the term of this patent is extended or adjusted under 35 U.S.C. 154(b) by 91 days.

(21) Appl. No.: 13/989,660

(22) PCT Filed: Dec. 15, 2011

(86) PCT No.: PCT/JP2011/007019
§ 371 (c)(1),
(2), (4) Date: Jul. 12, 2013

(87) PCT Pub. No.: WO2012/081254
PCT Pub. Date: Jun. 21, 2012

(65) Prior Publication Data
US 2013/0281724 A1    Oct. 24, 2013

(30) Foreign Application Priority Data

Dec. 17, 2010 (JP) ................. 2010-281787
Mar. 1, 2011  (JP) ................. 2011-044236
Mar. 1, 2011  (JP) ................. 2011-044386

(51) Int. Cl.
*C07F 3/06*    (2006.01)
*C08G 65/12*   (2006.01)

(52) U.S. Cl.
CPC .. *C07F 3/06* (2013.01); *C08G 65/12* (2013.01)

(58) Field of Classification Search
CPC ........................................ C07F 3/06
USPC .............. 556/2, 129; 585/16; 252/183.12
See application file for complete search history.

(56) References Cited

U.S. PATENT DOCUMENTS

| | | |
|---|---|---|
| 3,967,629 A | 7/1976 | Chappell et al. |
| 4,385,003 A | 5/1983 | Jung |
| 4,402,880 A | 9/1983 | Jung |
| 4,407,758 A | 10/1983 | Jung |
| 5,705,636 A | 1/1998 | Thomas et al. |
| 5,744,678 A | 4/1998 | Aida et al. |
| 2010/0062065 A1 | 3/2010 | Jo et al. |
| 2010/0291016 A1 | 11/2010 | Moretti |

FOREIGN PATENT DOCUMENTS

| | | |
|---|---|---|
| JP | 50-63148 A | 5/1975 |
| JP | 07-070056 A | 3/1995 |
| JP | 09-087206 A | 3/1997 |
| JP | 2003-300993 A | 10/2003 |
| JP | 2010-510982 A | 4/2010 |
| WO | 2009/093175 A1 | 7/2009 |

OTHER PUBLICATIONS

Eckehard V. Dehmlow et al., "On the Stereoselectivity of Iodocarbene and Carbenoid Additions to Cyclic Alkenes", Tetrahedron Letters, 1991, vol. 32, No. 43, pp. 6105-6108.
International Search Report, mailing date Mar. 6, 2012.
Teck-Peng Loh et al., "Nickel-Catalyzed Homoallylation Reaction of Aldehydes with 1,3-Dienes: Stereochemical and Mechanistic Studies", Organic Letters, 2002, vol. 4, No. 16, pp. 2715-2717.

*Primary Examiner* — Porfirio Nazario Gonzalez
(74) *Attorney, Agent, or Firm* — Arent Fox LLP (57) ABSTRACT

[Object]
To improve heat stability of diethylzinc which is used for a catalyst of polymerizing, an organic synthetic reaction reagent and a raw materials for providing a zinc film by MOCVD. And to offer the diethylzinc composition being superior in heat stability, even if it handles for a long term a metal zinc particle does not precipitate.
[Means for Solving Problem]
Use a diethylzinc composition added a compound which has particular carbon-carbon double bond to a diethylzinc.

21 Claims, 1 Drawing Sheet

DIETHYLZINC COMPOSITION, METHOD FOR HEAT STABILIZATION, AND COMPOUND FOR HEAT STABILIZATION

CROSS-REFERENCE TO RELATED APPLICATIONS

This application is a National Stage entry of International Application No. PCT/JP2011/007019, filed Dec. 15, 2011, which claims priority to Japanese Application Nos. 2010-281787, filed Dec. 17, 2010, 2011-044236 and 2011-044386, filed Mar. 1, 2011, the disclosure of these prior applications are hereby incorporated in their entirety by reference.

FIELD OF THE INVENTION

This invention relates to a diethylzinc composition superior in heat stability, a heat stabilization method and a compound for heat stabilization (thermo stabilization).

BACKGROUND ART

Diethylzinc is known as an extremely useful industrial material, for example as a catalyst for polymerizing a polyethylene oxide and a polypropylene oxide, an organic synthetic reaction reagent when manufacturing intermediates such as medicine or functional materials.

Also recently, as a method to form a zinc oxide film, a technique referred to as the MOCVD (Metal Organic Chemical Vapor Deposition) method is examined. In this method of approach, diethylzinc is used as a raw material and steam is used as an oxidizer.

A zinc oxide film provided by the MOCVD method has wide applications, that is, the zinc oxide film is used as a buffer layer of a CIGS solar battery, a transparent conductive film, an electrode membrane of a dye sensitization solar battery, a middle layer of a thin film Si solar battery, various function films in a solar battery such as a transparent conductive films, a photocatalyst film, a film intercepting ultraviolet rays, a film reflecting infrared rays, various function films such as antistatic films, a compound semiconductor light emitting element and electronic devices such as thin-film transistors.

It is known (e.g., non-patent document 1) that the diethylzinc gradually resolves by adding heat and precipitates zinc metal particles. Therefore, in the handling of the diethylzinc, there are problems of a fall off in product purity, pollution of a storage container and constriction of a production facility pipe. These are caused by the deposition of zinc metal particles formed by thermolysis.

As a method to solve the problems due to the deposition of the zinc metal precipitated by the above described thermolysis, a method is known which stabilizes the diethylzinc composition by adding compounds such as anthracene, acenaphthene, acenaphthylene (e.g., patent document (1)-(3)).

PRIOR ART

Patent Document

[Patent Document 1] U.S. Pat. No. 4,385,003
[Patent Document 2] U.S. Pat. No. 4,402,880
[Patent Document 3] U.S. Pat. No. 4,407,758

Non Patent Document

[Non Patent Document 1]
Yasuo Kuniya et Al. Applied Organometallic Chemistry, 5 vol. 337-347 pages, published 1991

DISCLOSURE OF INVENTION

Problems Solved by the Invention

As disclosed in Patent Document 1-3, even the addition of anthracene, acenaphthene or acenaphthelyne cannot stabilize diethylzinc sufficiently. Therefore a diethylzinc which is superior in heat stability is required.

Diethylzinc is important as a raw material in producing such as zinc oxide films by the MOCVD method. Generally, as a method to supply diethylzinc to external equipment such as coating equipment, feed a carrier gas such as nitrogen, argon, helium into a supply vessel which is filled with diethylzinc, and this causes the diethylzinc to exist as a saturated steam gas in the carrier gas.

Compounds such as anthracene, acenaphthene, acenaphthylene, which are known as additives to the diethylzinc, all these compounds have a higher boiling point than the boiling point of the diethylzinc (118 degrees Celsius), that is, the boiling point of anthracene is 342 degrees Celsius, acenaphthene is 279 degrees Celsius, acenaphthylene is 265-275 degrees Celsius.

Accordingly, stabilize the diethylzinc composition by adding anthracene, acenaphthene, or acenaphthylene, and supply the diethylzinc composition to the external equipment by the above described method over the long term. However, added anthracene, acenaphthene, or acenaphthylene accumulates in the diethylzinc left in the supply vessel, that is, there is a problem with the density of the anthracene, acenaphthene or acenaphthelyne becoming too high in the diethylzinc.

The purpose of the invention is to improve the heat stability of the diethylzinc which is used as a catalyst for polymerizing, an organic synthetic reaction reagent or a raw material for producing such as zinc oxide films by the MOCVD method. Also the purpose of the invention is to supply a diethylzinc composition which does not precipitate zinc metal particles over long term handling and is superior in heat stability.

Moreover, in the condition of feeding a carrier gas such as nitrogen, argon, helium into a supply vessel which is filled with the diethylzinc, the diethylzinc is caused to exist as a saturated steam gas in the carrier gas, and supply it to a piece of external equipment.

The purpose of the invention is to decrease the amount of the added compound which accumulates in the diethylzinc left in a supply vessel.

Means for Solving Problems

In order to solve the above mentioned problems, the inventors of the present invention researched and developed zealously. As a result, the inventors found that the heat stability of diethylzinc (CAS No. 557-20-0) improved remarkably by coexisting a compound having a particular carbon-carbon double bond with the diethylzinc.

And, in the condition of feeding a carrier gas such as nitrogen, argon, helium into a supply vessel which is filled with the diethylzinc, it causes the diethylzinc to exist as a saturated steam gas in the carrier gas, and supply it to an external piece of equipment, the inventors found that it become possible to decrease the amount of the added compound which accumulated in the diethylzinc left in a supply vessel.

Then the inventors completed the present invention.

A diethylzinc composition of the present invention is added to a compound as an additive which has carbon-carbon double bond of the following formula (1)

[Formula (1)]

(1)

In the formula (1), R represents respectively, hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms. (However, excluded when all of R is hydrogen).

Also, the compound which is represented in formula (1) includes at least one carbon frame represented in a following formula (2).

[Formula (2)]

(2)

And a diethylzinc composition of the present invention is added to a compound as an additive which has carbon-carbon double bond of the following formula (3)

[Formula (3)]

(3)

In the formula (3), R represents respectively, hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms. (However, excluded when all of R is hydrogen).

Also, the compound which is represented in formula (3) includes at least one carbon frame represented in a following formula (4).

[Formula (4)]

(4)

And a diethylzinc composition of the present invention is added to a compound as an additive which has carbon-carbon double bond of the following formula (5)

[Formula (5)]

(5)

In the formula (5), n is an integer from 1 to 4, R represents respectively, hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms.

And the diethylzinc composition of the present invention is added to a compound as an additive which has the carbon-carbon double bond of the following formula (6)

[Formula (6)]

(6)

In the formula (6), n is an integer from 1 to 4, R represents respectively, hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms.

A substituent group R coupled to the side chain of the compound having carbon-carbon double bond represented in the above-mentioned general formula (1), (3), (5) or (6).

The substituent group R represents respectively, hydrogen, a straight chain or branched alkyl group which has 1-8 carbon atoms such as a methyl group, an ethyl group, a propyl group, an isopropyl group and a butyl group, a straight chain or branched alkenyl group which has 1-8 carbon atoms such as a vinyl group, a propenyl group and an isopropenyl group, an allyl group which has 6-14 carbon atoms such as a phenyl group and a toluoyl group, a methoxy group, an ethoxy group, an isopropoxy group, a phenoxy group, an alkoxy group.

The number of the substituent group does not need to be the same number respectively, and it may be one two or more.

As a compound having carbon-carbon double bond represented with above-mentioned general formula (1) or (3), it can exemplify the following compounds. 2,4-dimethyl-1,3-pentadiene (CAS No. 1000-86-8), 2,4-dimethyl-1,3-hexadiene (CAS No. 10074-39-2), 2,4-dimethyl-1,3-heptadiene (CAS No. 20826-38-4), 2,4,5,5-tetramethyl-1,3-hexadiene (CAS No. 177176-57-7), 2,3,4-trimethyl-1,3-pentadiene (CAS No. 72014-90-5), 2,4-dimethyl-1,3,5-hexatriene (CAS No. 112369-48-9), 2,3,5-trimethyl-1,3,5-hexatriene (CAS No. 64891-79-8).

Among the compounds having carbon-carbon double bond represented by the formula (1) or (3), for example, 2,4-dimethyl-1,3-pentadiene (CAS No. 1000-86-8) which has a substituent group R, the substituent group R is hydrogen or a compound which has 3 or less number of carbon such as a methyl group, an ethyl group, an isopropyl group, an isopropenyl group, and the total number of carbon is 6-10, preferably 7-9.

The above 2,4-dimethyl-1,3-pentadiene is a liquid at room temperature, and the boiling point of the compound is close to the boiling point of diethyl zinc, that is 118 degrees Celsius.

Therefore, in the case that generating a saturated steam gas of diethylzinc by circulating a carrier gas such as nitrogen, argon, helium to the diethylzinc composition, and supply this saturated steam gas to an external piece of equipment, that is, when using the diethylzinc composition in the MOCVD method during a long period, it can prevent too much of the added compound from accumulating in the diethylzinc which remains in a supply vessel, and it becomes possible to coexist the additive in the diethylzinc at a moderate density level.

A compound having carbon-carbon double bond represented in the above-mentioned formula (5) has a cyclic hydrocarbon as a center frame, for example, if n=1, the center frame is 1,3-cyclohexadiene, if n=2, the center frame is 1,3-cycloheptadiene, if n=3, the center frame is 1,3-cyclooctadiene, if n=4, the center frame is 1,3-cyclononadiene.

Therefore, the compound of the present invention has a center frame of a cyclic hydrocarbon, and hydrogen or substituent group R couples to the center frame. That is, the compound of the present invention is 1,3-cyclohexadiene, 1,3-cycloheptadiene, 1,3-cyclooctadiene, 1,3-cyclononadiene, and the compounds those side chain are substituted with the substituent group R.

Note that, depending on the position of the substituent group R, the prefixal number 1,3-representing a position of the above-mentioned double bond may be changed to 2,4-, 3-5, in brief, it should include the structure of the formula (5).

Similarly, a compound having carbon-carbon double bond represented in the above-mentioned formula (6) has a cyclic hydrocarbon as a center frame, for example, if n=1, the center frame is 1,4-cyclohexadiene, if n=2, the center frame is 1,4-cycloheptadiene, if n=3, the center frame is 1,4-cyclo octadiene, if n=4, the center frame is 1,4-cyclononadiene.

Therefore, the compound of the present invention has a center frame of a cyclic hydrocarbon, and hydrogen or substituent group R couples to the center frame. That is, the compound of the present invention is 1,4-cyclohexadiene, 1,4-cycloheptadiene, 1,4-cyclooctadiene, 1,4-cyclononadiene, and the compounds those side chain are substituted with the substituent group R.

Note that, depending on a position of the substituent group R, the prefixal number 1,4-representing a position of the above-mentioned double bond may be changed to 2,5-, 3-6, in brief, it should include the structure of the formula (6).

The following compounds are exemplified in the above-mentioned formula (5) and (6).

1,3-cyclohexadiene, 1,4-cyclohexadiene, 1-methyl-1,4-cyclohexadiene, 2-methyl-1,4-cyclohexadiene, 3-methyl-1,4-cyclohexadiene, 4-methyl-1,4-cyclohexadiene, 5-methyl-1,4-cyclohexadiene, 1-methyl-1,3-cyclohexadiene, 3-methyl-1,3-cyclohexadiene, 4-methyl-1,3-cyclohexadiene, 5-methyl-1,3-cyclohexadiene, 2-methyl-1,3-cyclohexadiene, 2,4-dimethyl-1,4-hexadiene, 1,1-dimethyl-2,5-hexadiene, 1,3-dimethyl-1,3-cyclohexadiene, 2-methyl-1,3-cycloheptadiene, 5,5-dimethyl-1,4-cyclohexadiene, 1,2-dimethyl-1,3-cyclohexadiene, 1-ethyl-1,4-cyclohexadiene, α-terpinene, γ-terpinene, 1,3,5,5-tetramethyl-1,3-cyclohexadiene, 1,3,5,-trimethyl-1,4-cyclohexadiene, 1,3-cycloheptadiene, 1,4-cycloheptadiene, 2-methyl-1,3-cycloheptadiene, 1,3-cyclooctadiene, 1,4-cyclooctadiene, 1,3-cyclononadiene.

Among the compounds having carbon-carbon double bond represented with the formula (5) or (6), for example, 1-methyl-1,4-cyclohexadiene (CAS No. 4313-57-9) which has a substituent group R, the substituent group R is hydrogen or a compound which has 3 or less number of carbon such as a methyl group, an ethyl group, an isopropyl group, an isopropenyl group, and the total number of carbon is 6-10, preferably 7-9.

The above 1-methyl-1,4-cyclohexadiene is a liquid at room temperature, and the boiling point of the compound is close to the boiling point of diethylzinc, that is 118 degrees Celsius.

Therefore, in the case that generating a saturated steam gas of diethylzinc by circulating a carrier gas such as nitrogen, argon, helium to the diethylzinc composition, and supply this saturated steam gas to an external equipment, that is, when the diethylzinc composition is used in the MOCVD method over a long period, it can prevent too much added compound from accumulating in the diethylzinc which remains in a supply vessel, and it becomes possible to coexist the additive in the diethylzinc at a moderate density level.

As for the additive as used herein, sufficient effects are provided by independent addition, and a plural number of them may be mixed together.

Herein, concerning to the quantity of addition of the compound of the present invention which has carbon-carbon double bond and represented in a formula (1), (3), (5) and (6), there is no specific limitation on the quantity added as long as a performance of diethylzinc is maintained and a heat stabilization effect is provided.

Usually, when the ratio to diethylzinc is 50 ppm-20 wt %, preferably 100 ppm-10 wt %, more preferably 200 ppm-5 wt %, a diethylzinc composition superior in heat stability can be obtained.

If the quantity of the added compound of the present invention which has carbon-carbon double bond and represented in a formula (1), (3), (5) and (6) is too small sufficient heat stability improvement effects may not be provided, and if the quantity of addition of the compound is too much an effect to balance with quantity of addition is not provided.

Therefore, it is desirable to add an appropriate amount to obtain a desired effect with reference to heat stability.

As for the diethylzinc to be use for carrying out the present invention, diethylzinc generally known as an industrial material can be chosen, such as a polymerization catalyst of polyethylene oxide or polypropylene oxide, a reaction reagent for synthesizing an intermediate of medicine or functional materials.

Also, in the present invention, diethylzinc of a higher purity than that of the industrial material can be used too.

This high purity diethyl zinc is used to form a zinc oxide film by the MOCVD method. The zinc oxide film is applied as a buffer layer of a CIGS solar battery, a transparent conductive film, an electrode film of a dye sensitization solar battery, a middle layer of a film Si solar battery, various function films of the solar battery, a photocatalyst film, an ultraviolet rays interception film, an infrared reflection film, various function films such as antistatic films, a compound semiconductor light emitting element, an electronic devices such as thin-film transistors.

To prepare the diethylzinc composition of the present invention, the diethylzinc and the additive compound which has carbon-carbon double bond and represented in a formula (1), (3), (5) and (6) should be mixed.

And there is no specific limitation on how to mix them, the additive compound can merely be added to the diethyl zinc, for example, to attempt improvement of the preservation stability, the additive to the diethyl zinc can be added beforehand.

Also, for example, when the diethylzinc composition is used for a reaction, the additive to the diethylzinc may be added just before use.

And as for the temperature of the preparation of the diethylzinc composition of the present invention, 70 degrees Celsius or less are desirable since a thermolysis of the diethylzinc does not advance.

Usually, the preparation of the composition of the present invention can be performed at −20-35 degrees Celsius.

About the pressure force, there is no particular limit either, usually, the diethylzinc and the composition of the present invention can be prepared at around atmospheric pressure such as 0.1013 MPa except in a special case such as reaction.

Concerning the machine parts and the atmosphere for using a storage container, a transportation container, a storage tank and a facility such as the pipe for the diethylzinc composition of the present invention, the facilities and atmosphere used for diethyl zinc can simply be converted.

For example, SUS, carbon steel, titanium, a metal such as Hastelloy, teflon (registered trademark) and resin such as a fluorine-based rubber are applicable as materials of the above mentioned machine parts.

Also, regarding the atmosphere, inert gases such as nitrogen, helium, argon as in the case of the diethylzinc can be used.

And the diethylzinc composition of the present invention can dissolve in a well-known solvent which can be used for dissolving the diethylzinc. The following are examples of the solvent.

A saturated hydrocarbon such as pentane, hexane, heptane and octane, an aromatic hydrocarbon such as benzene, toluene and xylene, an ether-based compounds such as a diethyl ether, isopropyl ether, tetrahydrofuran, dioxane or diglyme.

As for the application of the diethylzinc composition of the present invention, it is similar to the application of the diethylzinc as used conventionally.

That is for example, a polymerization catalyst of polyethylene oxide or polypropylene oxide, a reaction reagent of synthesizing an intermediate of medicine or functional materials. Also, the diethylzinc composition of the present invention can be applied to form a zinc oxide film by the MOCVD method. The zinc oxide film is applied as a buffer layer of a CIGS solar battery, a transparent conductive film, an electrode film of a dye sensitization solar battery, a middle layer of a film Si solar battery, various function films of the solar battery, a photocatalyst film, an ultraviolet rays interception film, an infrared reflection film, various function films such as antistatic films, a compound semiconductor light emitting element, application for forming an oxide used in an electronic devices such as thin-film transistor, application for forming a film of an electronic devices of II-VI group such as ZnS.

Effects of the Invention

The diethylzinc composition of the present invention added to a compound having carbon-carbon double bond represented in a general formula (1), (3), (5) or (6) is superior in heat stability, and the deposition of zinc metal particles is extremely small, then it can prevent a fall off in product purity, pollution of the storage container and a constriction of the production facility pipe.

And particularly, for example, in the case of carrying out the MOCVD method, when generating a saturated steam gas of the diethylzinc by circulating a carrier gas such as a nitrogen, argon, helium to the diethylzinc composition, and supplying this saturated steam gas to an external piece of equipment, the boiling point of the compound of the present invention is close to the boiling point of diethylzinc, even if the diethylzinc composition of the invention is supplied over the long term, it can prevent the added compound from accumulating in the diethylzinc composition remained in a supply vessel.

BEST MODE FOR CARRYING OUT INVENTION

The present invention is explained below in detail with embodiments, these embodiments do not limit the present invention.

[Measuring Equipment]

DSC (Differential Scanning Calorimetry) measurement was carried out using a DSC6200 (made by SEIKO Instruments Co., Ltd.)

When an additive of the present invention is obtained by composition, $^1$H-NMR measurement was carried out using a Gemini-300 (made by Varian Corporation), GC-MS measurement was carried out using an HP6890 (made by Hewlett-Packard Packard Corporation)

[Preparation of the Diethyl Zinc Composition-1]

Diethylzinc (made by TOSOH FINECHEM Corporation) and 2,4-dimethyl-1,3-pentadiene (CAS No. 1000-86-8) (commercial reagent) were weighted in a glass container by predetermined density under a nitrogen atmosphere at room temperature.

A diethylzinc composition was then prepared by dissolving the additive (2,4-dimethyl-1,3-pentadiene) into the diethyl zinc.

[Preparation of the Diethyl Zinc Composition-2]

Diethylzinc (made by TOSOH FINECHEM Corporation) and 1-methyl-1,4-cyclohexadiene (CAS No. 4313-57-9) (commercial reagent) were weighted in a glass container by predetermined density under a nitrogen atmosphere at room temperature.

A diethylzinc composition was then prepared by dissolving the additive in the diethyl zinc.

The addition rate of the additive to diethylzinc (weight percent) is calculated using the following formula.

Addition rate (weight percent) of the additive=(additive weight/(additive weight+diethyl zinc weight))×100

To the diethylzinc composition prepared by the above-mentioned method. The heat stabilization effect of the additive was evaluated by carrying out DSC measurement (Differential Scanning Calorimetry).

[Reference 1]

[Heat Stabilization Examination by DSC Measurement to Diethyl Zinc]

Under a nitrogen atmosphere, weighted the diethylzinc and sealed in a DSC cell made of SUS.

Carried out a thermal analysis on the provided sample by the DSC method, the measurement temperature range was 30-450 degrees Celsius, and the rise speed of temperature was 10 degrees Celsius/minute.

The resolution temperature of each sample is observed at initial exothermic temperature of DSC measurement.

The initial exothermic temperature of the sample of diethylzinc which is not added an additive is shown in Table 1.

Example 1

Heat Stabilization Examination by DSC Measurement to Diethylzinc Composition

Similarly to Reference 1, under a nitrogen atmosphere, weighted the diethylzinc composition added 2,4-dimethyl-1,3-pentadiene (CAS No. 1000-86-8) which is a compound of the present invention, and sealed in a DSC cell made of SUS. Similarly to Reference 1, carried out a thermal analysis to the provided samples by DSC method, the measurement temperature range was 30-450 degrees Celsius, and the rise speed of temperature was 10 degrees Celsius/minute. The initial exothermic temperatures of the samples of diethylzinc composition are shown in Table 1.

The initial exothermic temperature of the sample of the diethylzinc composition which added a compound of the present invention is higher than the initial exothermic temperature of the sample of diethylzinc only provided by the reference, and the start temperature of the resolution of the composition of the present invention is higher than the start temperature of the sample of diethylzinc only.

From this result, it is confirmed that the diethylzinc composition which was added to an additive has a superior heat stability.

Also, the boiling point of 2,4-dimethyl-1,3-pentadiene which is a compound of the present invention is 93 degrees Celsius, this boiling point is lower than the boiling point, 118 degrees Celsius, of the diethylzinc, therefore in the case of carrying out the MOCVD method, when generating a saturated steam gas of the diethylzinc by circulating a carrier gas such as nitrogen, argon, helium to the diethylzinc composition, supplying this saturated steam gas to an external piece of equipment, and when supply the diethyl zinc composition of the invention over the long term, it can prevent the added compound from accumulating in the diethyl zinc composition remaining in a supply vessel.

Comparative Example 1-3

Similarly to Example 1, carried out the examination to the diethylzinc composition which was added to anthracene, acenaphthene and -acenaphthylene, these are the compounds as described in Prior art 1-3.

The initial exothermic temperatures of the samples are shown in Table 1.

The initial exothermic temperature of these samples is lower than the initial exothermic temperature of the sample of the diethylzinc composition which was added to a compound of the present invention, therefore, the composition which was added to a conventional additive is inferior to a composition of the present invention in heat stability.

And the boiling point of anthracene is 342 degrees Celsius, the boiling point of acenaphthene is 279 degrees Celsius and the boiling point of acenaphthylene is 265-275 degrees Celsius, those boiling points are higher than 118 degrees Celsius which is the boiling point of diethylzinc.

Therefore in the case of carrying out the MOCVD method, when generating a saturated steam gas of the diethyl zinc by circulating a carrier gas such as a nitrogen, argon, helium to the diethylzinc composition, supplying this saturated steam gas to an external piece of equipment, and when supplying the conventional diethylzinc composition over the long term, a problem occurs in that those compounds accumulate in a diethylzinc composition remaining in a supply vessel.

Example 2-6

Heat Stabilization Examination by DSC Measurement to Diethylzinc Composition

Similarly to Example 1, carried out the same examination to the diethylzinc composition, except changing the addition density of 2,4-dimethyl-1,3-pentadiene (CAS No. 1000-86-8) which is a compound of the present invention. The initial exothermic temperatures of the samples are shown in Table 1.

Even if it lowers the addition density of the compound, the initial exothermic temperature of the sample of the diethylzinc composition which was added to a compound of the present invention is higher than the initial exothermic temperature of the sample of diethylzinc only provided by the reference.

From this result, it is ensured that the diethylzinc composition which was added to an additive has a superior heat stability.

Comparative Example 4-6

Similarly to Example 3, carried out the examination to the diethylzinc composition which it added anthracene, acenaphthene and acenaphthylene, these are the compounds as described in Prior art 1-3. The initial exothermic temperatures of the samples are shown in Table 1.

The initial exothermic temperature of these samples is lower than the initial exothermic temperature of the sample of the diethylzinc composition which was added to a compound of the present invention, therefore, the composition which was added to a conventional additive is inferior to a composition of the present invention in heat stability.

TABLE 1

| Example | Diethylzinc composition | Additive | Ratio of the additive (%) | DSC sample quantity (mg) | DSC initial exothermic temperature (° C.) | Boiling temperature of the additive (° C.) |
| --- | --- | --- | --- | --- | --- | --- |
| Reference 1 | Diethylzinc | None | 0 | 2.7 | 182.9 | None |
| Example 1 | Diethylzinc-2,4-Dimethyl-1,3-Pentadiene | 2,4-Dimethyl-1,3-Pentadiene | 4.0 | 2.6 | 213.4 | 93 |
| Example 2 | Diethylzinc-2,4-Dimethyl-1,3-Pentadiene | 2,4-Dimethyl-1,3-Pentadiene | 1.0 | 2.5 | 205.2 | 93 |
| Example 3 | Diethylzinc-2,4-Dimethyl-1,3-Pentadiene | 2,4-Dimethyl-1,3-Pentadiene | 0.50 | 2.5 | 202.6 | 93 |

TABLE 1-continued

| Example | Diethylzinc composition | Additive | Ratio of the additive (%) | DSC sample quantity (mg) | DSC initial exothermic temperature (° C.) | Boiling temperature of the additive (° C.) |
|---|---|---|---|---|---|---|
| Example 4 | Diethylzinc-2,4-Dimethyl-1,3-Pentadiene | 2,4-Dimethyl-1,3-Pentadiene | 0.10 | 2.6 | 201.2 | 93 |
| Example 5 | Diethylzinc-2,4-Dimethyl-1,3-Pentadiene | 2,4-Dimethyl-1,3-Pentadiene | 0.05 | 2.5 | 194.0 | 93 |
| Example 6 | Diethylzinc-2,4-Dimethyl-1,3-Pentadiene | 2,4-Dimethyl-1,3-Pentadiene | 0.02 | 2.5 | 188.0 | 93 |
| Comparative Example 1 | Diethylzinc-Anthracene | Anthracene | 4.36 | 3.3 | 188.7 | 342 |
| Comparative Example 2 | Diethylzinc-Acenaphthylene | Acenaphthylene | 4.43 | 3.4 | 173.5 | 265~275 |
| Comparative Example 3 | Diethylzinc-Acenaphthene | Acenaphthene | 4.27 | 1.8 | 201.9 | 279 |
| Comparative Example 4 | Diethylzinc-Anthracene | Anthracene | 0.48 | 2.7 | 187.0 | 342 |
| Comparative Example 5 | Diethylzinc-Acenaphthylene | Acenaphthylene | 0.49 | 2.8 | 171.9 | 265~275 |
| Comparative Example 6 | Diethylzinc-Acenaphthene | Acenaphthene | 0.50 | 2.7 | 175.9 | 279 |

Example 7-14

Heat Stabilization Examination by DSC Measurement to Diethylzinc Composition

Similarly to Example 1, carried out a thermal analysis to the diethylzinc composition added compound of the present invention in various ratios, the compound is a mixture including dimethyl hexadiene, a mixture including trimethyl hexadiene or 2,6-dimethyl-2,4,6-octatriene (CAS No. 673-84-3). The initial exothermic temperature of the samples are shown in Table 2.

Even the addition density of the compound is lowered, the initial exothermic temperature of the samples of the diethylzinc composition which was added to a compound of the present invention is higher than the initial exothermic temperature of the sample of diethylzinc only provided by the reference.

From this result, it is certain that the diethylzinc composition which added the additive has a superior heat stability.
[Reference 2]

The mixture including the dimethylhexadiene and the mixture including the trimethylhexadiene those are the compounds of the present invention, and those compounds are synthesized taking well-known composition technique of 2,4-dimethyl-1,3-pentadiene (CAS No. 1000-86-8) into account.

The mixture including the dimethylhexadiene and the mixture including the trimethylhexadiene are refined by distillation refinement.

In the distillation refinement (atmospheric pressure) of the crude product including the above-mentioned mixture, when the distillation fraction including each mixture distills, the bottom heating temperature of the mixture including the dimethylhexadiene was 140 degrees Celsius, the bottom heating temperature of the mixture including the trimethylhexadiene was 165 degrees Celsius, therefore, the boiling point of each mixture is lower than a bottom heating temperature.

Figure 1:
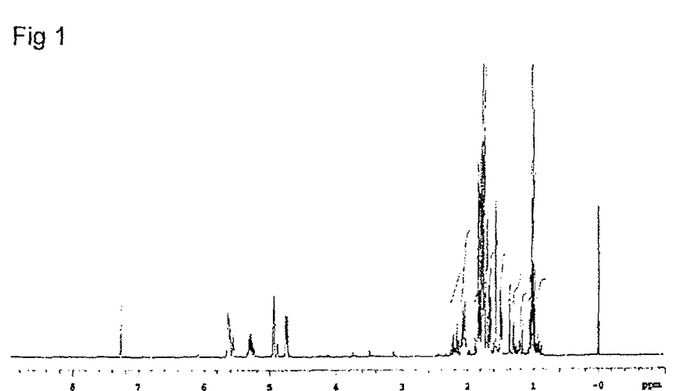
FIG. 1 NMR chart of the mixture including a dimethyl hexadiene (solvent: $CDCl_3$)
Figure 2:
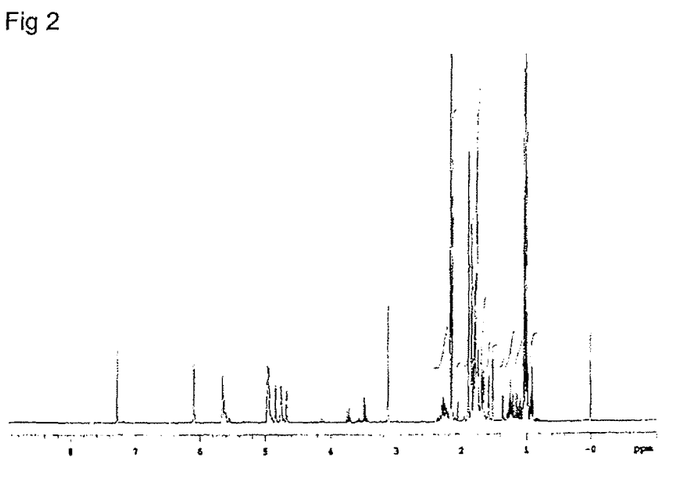
FIG. 2 NMR chart of the mixture including a trimethyl hexadiene (solvent: $CDCl_3$)

The mixture including the dimethylhexadiene and the mixture including the trimethylhexadiene are analyzed by $^1$H-NMR measurement and GC-MS measurement. Each NMR chart of the mixtures is shown in FIGS. 1 and 2.

Note that a commercial reagent is used for 2,6-dimethyl-2,4,6-octatriene (CAS No. 673-84-3).

TABLE 2

| Example | Diethylzinc composition | Additive | Ratio of the additive (%) | DSC sample quantity (mg) | DSC initial exothermic temperature (° C.) | Boiling temperature of the additive (° C.) |
|---|---|---|---|---|---|---|
| Example 7 | Diethylzinc-A mixture including a dimethylhexadiene | A mixture including a dimethylhexadiene | 0.10 | 2.2 | 190.5 | <140 |
| Example 8 | Diethylzinc-A mixture including a dimethylhexadiene | A mixture including a dimethylhexadiene | 1.00 | 2.5 | 200.6 | <140 |
| Example 9 | Diethylzinc-A mixture including a dimethylhexadiene | A mixture including a dimethylhexadiene | 4.00 | 2.0 | 207.6 | <140 |
| Example 10 | Diethylzinc-A mixture including a dimethylhexadiene | A mixture including a trimethylhexadiene | 1.00 | 3.0 | 201.4 | <165 |
| Example 11 | Diethylzinc-A mixture including a trimethylhexadiene | A mixture including a trimethylhexadiene | 4.00 | 2.3 | 210.5 | <165 |
| Example 12 | Diethylzinc-2,6-Dimethyl-2,4,6-Octatriene | 2,6-Dimethyl-2,4,6-Octatriene | 0.50 | 2.1 | 193.8 | <200 |

TABLE 2-continued

| Example | Diethylzinc composition | Additive | Ratio of the additive (%) | DSC sample quantity (mg) | DSC initial exothermic temperature (° C.) | Boiling temperature of the additive (° C.) |
|---|---|---|---|---|---|---|
| Example 13 | Diethylzinc-2,6-Dimethyl-2,4,6-Octatriene | 2,6-Dimethyl-2,4,6-Octatriene | 1.00 | 2.0 | 198.1 | <200 |
| Example 14 | Diethylzinc-2,6-Dimethyl-2,4,6-Octatriene | 2,6-Dimethyl-2,4,6-Octatriene | 4.29 | 2.3 | 203.1 | <200 |

*Among the boiling temperature of the additive in the table, Examples 7-11 are the bottom heating temperature when the distillation fraction including the additive distills at distillation refinement of each additive.

Example 15

Heat Stabilization Examination by DSC Measurement to Diethylzinc Composition

Similarly to Reference 1, under nitrogen atmosphere, weighted the diethylzinc composition added 1-methyl-1,4-cyclohexadiene (CAS No 0.4313-57-9) (commercial reagent) which is a compound of the present invention, and sealed in DSC cell made of SUS.

Similarly to Reference 1, carried out a thermal analysis to the provided samples by DSC method, the measurement temperature range was 30-450 degrees Celsius, and the rise speed of temperature was 10 degrees Celsius/minute. The initial exothermic temperature of the samples are shown in Table 3.

The initial exothermic temperature of the sample of the diethylzinc composition which was added to a compound of the present invention is higher than the initial exothermic temperature of the sample of diethylzinc only provided by the reference, and the start temperature of the resolution of the composition of the present invention is higher than the start temperature of the sample of diethylzinc only.

From this result, it is proved that the diethylzinc composition which was added to an additive has superior heat stability.

Also, the boiling point of 1-methyl-1,4-cyclohexadiene is 115 degrees Celsius, this boiling point is lower than the boiling point, 118 degrees Celsius, of the diethylzinc, therefore in the case of carrying out the MOCVD method, when generating a saturated steam gas of the diethylzinc by circulating a carrier gas such as nitrogen, argon, helium to the diethylzinc composition, supplying this saturated steam gas to an external piece of equipment, and when supplying the diethylzinc composition of the invention over the long term, the added compound can be prevented from accumulating in the diethylzinc composition remained in a supply vessel.

Example 16-18

Similarly to Example 1, carried out a thermal analysis to the diethylzinc composition changing the addition density of 1-methyl-1,4-cyclohexadiene (CAS No 0.4313-57-9) (commercial reagent) which is a compound of the present invention. The initial exothermic temperature of the samples are shown in Table 3.

Even if the addition density of the compound is lowered, the initial exothermic temperature of the samples of the diethylzinc composition which was added to a compound of the present invention is higher than the initial exothermic temperature of the sample of diethylzinc only provided by the reference. From this result, it is proved that the diethylzinc composition which added the additive has a superior heat stability.

Example 19-22

As embodiments of the additives of the present invention, select 1,4-cyclohexadiene (CAS No. 628-41-1), α-terpinene (CAS No. 99-86-5), γ-terpinene (CAS No. 99-85-4) and 1,3,5,5-tetramethyl-1,3-cyclohexadiene (CAS No. 4724-89-4) (all commercial reagent), and prepare the diethylzinc composition using above additives, then carried out a thermal analysis to the diethylzinc composition similarly to Example 1. The initial exothermic temperature of the samples are shown in Table 3.

The initial exothermic temperature of the sample of the diethylzinc composition which added a compound of the present invention is higher than the initial exothermic temperature of the sample of diethylzinc only provided by the reference, and the start temperature of the resolution of the composition of the present invention is higher than the start temperature of the sample of diethylzinc only.

From this result, it is ensured that the diethylzinc composition which added an additive has superior heat stability.

Also, the boiling point of the compound of the present invention is lower than the well-known compound, therefore in the case of carrying out MOCVD method, when generate a saturated steam gas of the diethylzinc by circulating a carrier gas such as nitrogen, argon, helium to the diethylzinc composition, and supplying this saturated steam gas to an external piece of equipment, and when supplying the diethylzinc composition of the invention over the long term, the added compound can be prevented from accumulating in the diethylzinc composition remained in a supply vessel.

TABLE 3

| Example | Diethylzinc composition | Additive | Ratio of the additive (%) | DSC sample quantity (mg) | DSC initial exothermic temperature (° C.) | Boiling temperature of the additive (° C.) |
|---|---|---|---|---|---|---|
| Reference 1 | Diethylzinc | None | 0 | 2.7 | 182.9 | None |
| Example 15 | Diethylzinc-1-Methyl-1,4-Cyclohexadiene | 1-Methyl-1,4-Cyclohexadiene | 4.29 | 2.3 | 203.1 | 115 |
| Example 16 | Diethylzinc-1-Methyl-1,4-Cyclohexadiene | 1-Methyl-1,4-Cyclohexadiene | 1.00 | 2.1 | 198.1 | 115 |

TABLE 3-continued

| Example | Diethylzinc composition | Additive | Ratio of the additive (%) | DSC sample quantity (mg) | DSC initial exothermic temperature (° C.) | Boiling temperature of the additive (° C.) |
|---|---|---|---|---|---|---|
| Example 17 | Diethylzinc-1-Methyl-1,4-Cyclohexadiene | 1-Methyl-1,4-Cyclohexadiene | 0.50 | 2.4 | 199.2 | 115 |
| Example 18 | Diethylzinc-1-Methyl-1,4-Cyclohexadiene | 1-Methyl-1,4-Cyclohexadiene | 0.10 | 2.1 | 194.9 | 115 |
| Example 19 | Diethylzinc-1,4-Cyclohexadiene | 1,4-Cyclohexadiene | 4.00 | 2.2 | 204.8 | 88 |
| Example 20 | Diethylzinc-α-Terpinene | α-Terpinene | 4.00 | 2.0 | 199.2 | 173-175 |
| Example 21 | Diethylzinc-γ-Terpinene | γ-Terpinene | 4.00 | 2.2 | 201.3 | 183 |
| Example 22 | Diethylzinc-1,3,5,5-Tetramethyl-1,3-Cyclohexadiene | 1,3,5,5-Tetramethyl-1,3-Cyclohexadiene | 4.00 | 2.4 | 203.4 | 162 |
| Comparative Example 1 | Diethylzinc-Anthracene | Anthracene | 4.36 | 3.3 | 188.7 | 342 |
| Comparative Example 2 | Diethylzinc-Acenaphthylene | Acenaphthylene | 4.43 | 3.4 | 173.5 | 265~275 |
| Comparative Example 3 | Diethylzinc-Acenaphthene | Acenaphthene | 4.27 | 1.8 | 201.9 | 279 |
| Comparative Example 4 | Diethylzinc-Anthracene | Anthracene | 0.48 | 2.7 | 187.0 | 342 |
| Comparative Example 5 | Diethylzinc-Acenaphthylene | Acenaphthylene | 0.49 | 2.8 | 171.9 | 265~275 |
| Comparative Example 6 | Diethylzinc-Acenaphthene | Acenaphthene | 0.50 | 2.7 | 175.9 | 2.79 |

The invention claimed is:

1. A diethylzinc composition comprising a compound as an additive, the compound comprising a carbon-carbon double bond of the following formula (1)

[Formula (1)]

(1)

wherein each R represents independently, a hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms, and wherein the compound which is represented in formula (1) comprises at least one carbon frame represented in a following formula (2)

[Formula 2)]

(2)

wherein a ratio of the additive to diethylzinc is 50 ppm-20 wt %.

2. A diethylzinc composition comprising a compound as an additive, the compound comprising a carbon-carbon double bond of the following formula (3)

[Formula (3)]

(3)

wherein each R represents independently, a hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms, wherein the compound which is represented in formula (3) comprises at least one carbon frame represented in a following formula (4)

[Formula (4)]

(4)

wherein a ratio of the additive to diethylzinc is 50 ppm-20 wt %.

3. The diethylzinc composition according to claim 1, wherein R is a hydrogen or a compound which has 3 or less carbon atoms, and the total number of carbon atoms is 6-10.

4. A method of heat stabilization of a diethylzinc composition, wherein using the compound as an additive claimed in claim 1, and adding the additive with a ratio of the additive to diethylzinc of 50 ppm-20 wt %.

5. A composition having a structure as an additive improving heat stability of diethylzinc claimed in claim 1.

6. The diethylzinc composition according to claim 1, comprising further additives, wherein the further additives are independently a saturated or an unsaturated hydrocarbon comprising 5-25 carbon atoms, an aromatic hydrocarbon compound comprising 6-30 carbon atoms or an ether-based compound.

7. The method according to claim 4, wherein the diethylzinc composition comprises further additives, wherein the further additives are independently a saturated or unsaturated hydrocarbon comprising 5-25 carbon atoms, an aromatic hydrocarbon compound comprising 6-30 carbon atoms or an ether-based compound.

8. The diethylzinc composition according to claim 5 comprising further additives, wherein the further additives are independently a saturated or unsaturated hydrocarbon comprising 5-25 carbon atoms, an aromatic hydrocarbon compound comprising 6-30 carbon atoms or an ether-based compound.

9. A diethylzinc composition comprising a compound as an additive which has a carbon-carbon double bond of the following formula (5)

[Formula (5)]

(5)

wherein n is an integer from 1 to 4, each R represents independently, a hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms, wherein a ratio of the additive to diethylzinc is 50 ppm-20 wt %.

10. A diethylzinc composition comprising a compound as an additive which has a carbon-carbon double bond of the following formula (6)

[Formula (6)]

(6)

wherein n is an integer from 1 to 4, each R represents independently, a hydrogen, a straight chain or branched alkyl group which has 1-8 carbon atoms, a straight chain or branched alkenyl group which has 1-8 carbon atoms, an allyl group which has 6-14 carbon atoms, a straight chain or branched alkoxy group which has 1-8 carbon atoms.

11. The diethyizinc composition according to claim 9, wherein R is a hydrogen or a compound which has 3 or less carbon atoms, and the total number of carbon atoms is 6-10.

12. A method of heat stabilization of a diethylzinc composition, wherein using the compound as an additive claimed in claim 9, and adding the additive with a ratio of the additive to diethylzinc of 50 ppm-20 wt %.

13. The diethylzinc composition according to claim 2, wherein R is a hydrogen or a compound which has 3 or less carbon atoms, and the total number of carbon atoms is 6-10.

14. A method of heat stabilization of a diethylzinc composition, wherein using the compound as an additive claimed in claim 2, and adding the additive with a ratio of the additive to diethylzinc of 50 ppm-20 wt %.

15. A composition having a structure as an additive improving heat stability of diethylzinc claimed in claim 2.

16. The diethylzinc composition according to claim 2, comprising further additives, wherein the further additives are independently a saturated or unsaturated hydrocarbon comprising 5-25 carbon atoms, an aromatic hydrocarbon compound comprising 6-30 carbon atoms or an ether-based compound.

17. The method according to claim 14, wherein the diethylzinc composition comprises further additives, wherein the further additives are independently a saturated or unsaturated hydrocarbon comprising 5-25 carbon atoms, an aromatic hydrocarbon compound comprising 6-30 carbon atoms or an ether-based compound.

18. AThe diethylzinc composition according to claim 15, comprising further additives, wherein the further additives are independently a saturated or unsaturated hydrocarbon comprising 5-25 carbon atoms, an aromatic hydrocarbon compound comprising 6-30 carbon atoms or an ether-based compound.

19. The diethylzinc composition according to claim 11, wherein R is a hydrogen or a compound which has 3 or less carbon atoms, and the total number of carbon atoms is 6-10.

20. The diethylzinc composition according to claim 10, wherein a ratio of the additive to diethylzinc is 50 ppm-20 wt %.

21. A method of heat stabilization of a diethylzinc composition, wherein using the compound as an additive claimed in claim 10, and adding the additive with a ratio of the additive to diethylzinc of 50 ppm-20 wt %.

* * * * *